United States Patent
Bernstein et al.

(10) Patent No.: US 10,101,496 B2
(45) Date of Patent: Oct. 16, 2018

(54) INJECTION WELL IDENTIFICATION USING TRACER PARTICLES

(71) Applicant: The Charles Stark Draper Laboratory, Inc., Cambridge, MA (US)

(72) Inventors: Jonathan J. Bernstein, Medfield, MA (US); Julio C. Guerrero, Cambridge, MA (US); Mitchell Hansberry, Southborough, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 43 days.

(21) Appl. No.: 15/379,468

(22) Filed: Dec. 14, 2016

(65) Prior Publication Data

US 2017/0097443 A1 Apr. 6, 2017

Related U.S. Application Data

(63) Continuation of application No. PCT/US2015/036135, filed on Jun. 17, 2015.

(60) Provisional application No. 62/015,713, filed on Jun. 23, 2014.

(51) Int. Cl.
*G01V 5/00* (2006.01)
*G01V 15/00* (2006.01)
*G01V 5/12* (2006.01)
*E21B 47/10* (2012.01)
*E21B 43/16* (2006.01)

(52) U.S. Cl.
CPC .............. *G01V 15/00* (2013.01); *E21B 43/16* (2013.01); *E21B 47/1015* (2013.01); *G01V 5/125* (2013.01)

(58) Field of Classification Search
CPC .............................. G01V 15/00; G01V 5/125
See application file for complete search history.

(56) References Cited

U.S. PATENT DOCUMENTS 5,283,079 A * 2/1994 Wang ................. B01J 8/008
427/128
7,938,203 B1 * 5/2011 Hall .................. B01D 17/0217
175/107

(Continued)

OTHER PUBLICATIONS

International Searching Authority—International Search Report—International Application No. PCT/US2015/036135 dated Mar. 15, 2016, together with the Written Opinion of the International Searching Authority, 15 pages.

*Primary Examiner* — Yara B Green
(74) *Attorney, Agent, or Firm* — Sunstein Kann Murphy & Timbers LLP

(57) ABSTRACT

A system and method of injection well identification using tracer particles is disclosed. A collector-reader for analyzing magnetic particles in a fluid that is moving with respect to the collector-reader includes an array of magnets whose magnetization direction is varied so as to create regions of high magnetic field gradient in the fluid, a stopper configured to concentrate spatially the particles attracted to the array, and a reader including a source configured to excite the particles concentrated by the stopper and a detector configured to capture a particle excitation signature emitted by the magnetic particles. A method for observing a subterranean reservoir penetrated by a production well and two or more injection wells is also disclosed.

15 Claims, 13 Drawing Sheets

(56) References Cited

U.S. PATENT DOCUMENTS

| | | | |
|---|---|---|---|
| 2009/0087911 A1* | 4/2009 | Ramos | E21B 47/1015 |
| | | | 436/27 |
| 2009/0088336 A1 | 4/2009 | Burd et al. | |
| 2009/0151939 A1 | 6/2009 | Bailey et al. | |
| 2010/0303716 A1* | 12/2010 | Jin | A61M 37/0092 |
| | | | 424/1.11 |
| 2010/0314108 A1 | 12/2010 | Crews et al. | |
| 2013/0197296 A1* | 8/2013 | Ott | A61N 2/004 |
| | | | 600/12 |
| 2013/0264248 A1* | 10/2013 | Smolkin | B03C 1/18 |
| | | | 209/214 |
| 2015/0068806 A1* | 3/2015 | Duran Toro | E21B 49/00 |
| | | | 175/50 |

* cited by examiner

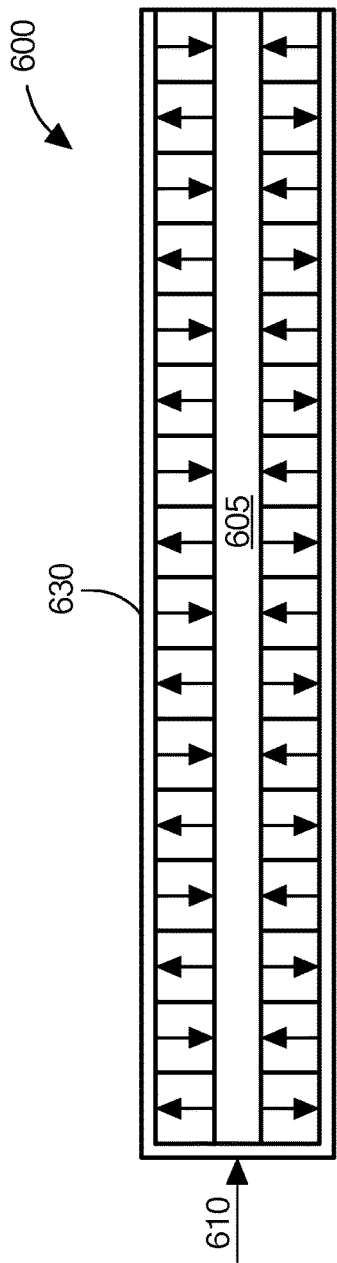
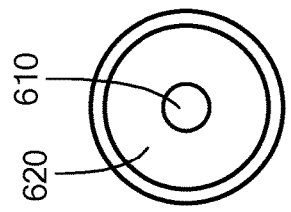
FIG. 14
FIG. 15

INJECTION WELL IDENTIFICATION USING TRACER PARTICLES

CROSS REFERENCE TO RELATED APPLICATIONS

This application is a continuation of International Application No. PCT/US2015/036135 filed on Jun. 17, 2015, which claims the benefit of U.S. Provisional Patent Application No. 62/015,713 filed on Jun. 23, 2014, the disclosures of which are incorporated by reference herein in their entirety.

TECHNICAL FIELD

The present invention relates to the use of tracers within subterranean reservoirs and, more particularly, to injection well identification using X-ray fluoroscopy or other analogous analytical techniques applied to tracer particles.

BACKGROUND

Various industries inject fluids into the ground for the purposes of extraction of natural resources from underground reservoirs. Some examples include: 1) fracking; 2) stimulation of oil wells by injecting $CO_2$ and/or water via injection wells into producing wells; 3) stimulation of heavy oil wells by inserting fluids that run in wells parallel to the production well; 4) stimulation by injecting steam; 5) secondary recovery of hydrocarbons (oil and gas); and 6) In-Situ Recovery ("ISR") of uranium, etc. In some cases, multiple injection wells and one or more producing wells tap a subterranean reservoir. Fluid from an injection well may flow through to a production well. It is often desirable to know from which injection well the fluid originated. In other cases, fluids from an injection well may be a source of contamination, such as drinking water contamination. It is often desired to determine the origin of the contamination.

SUMMARY OF THE EMBODIMENTS

In one embodiment, a collector-reader for analyzing magnetic particles in a fluid that is moving with respect to the collector-reader includes an array of magnets whose magnetization direction is varied so as to create regions of high magnetic field gradient in the fluid, a stopper configured to concentrate spatially the particles attracted to the array, and a reader including a source configured to excite the particles concentrated by the stopper and a detector configured to capture a particle excitation signature emitted by the magnetic particles.

The adjacent magnets in the array may have opposite magnetization polarity or may be configured as a Halbach array. The source may excite the particles with X-rays and the detector may measure the resulting particle X-ray fluorescence. The collector-reader may further include a window transparent to X-rays adjacent to the stopper. The source may excite the particles optically and the detector may measure the resulting optical fluorescence. The source may excite the particles and the detector may measure particle excitation using one or more of: X-ray fluorescence, optical fluorescence, atomic absorption, atomic spectroscopy, neutron activation, inductively coupled plasma mass spectrometry, and X-ray photo-electron spectroscopy. The stopper may be v-shaped. The array may be configured to be suspended in the fluid. The array may be configured as a disk with an axis and the disk includes fins that spin the disk on the axis when impacted by the fluid. The array may be configured as a collar surrounding a non-magnetic section of a pipe, an axis of the array and an axis of the pipe coincident, and wherein the array is configured to rotate on its axis. The collector-reader may further include a cleaner that removes magnetic particles from the stopper. The cleaner may be a protuberance on an inner surface of the non-magnetic section of the pipe. The reader may be at least 10 feet from the array.

In another embodiment, a collector-reader for analyzing magnetic particles in a fluid that is moving with respect to the collector-reader includes a linear array of magnets wherein adjacent magnets in the array have opposite polarity, a removable sheath surrounding the array, the sheath configured to capture the particles attracted to the array, and a reader including a source configured to excite the particles captured by the sheath and a detector configured to capture a particle excitation signature emitted by the magnetic particles.

In another embodiment, a method for observing a subterranean reservoir penetrated by a production wellbore and two or more injection wellbores is provided. A first set of tracer particles is delivered to the reservoir by one injection wellbore, while a second set of tracer particles is delivered to the reservoir via a second injection wellbore. The first set of tracer particles includes a first identification element while the second set of tracer particles includes a second identification element. Each tracer particle includes a magnetic material. The presence or absence of particles from the first set or second set of tracer particles in fluid produced from the production well is determined by X-ray fluorescence ("XRF") spectroscopy or another analogous analytical technique using the identification elements in the production fluid. The fluid flow (or absence thereof) from a particular injection well and the production well can thus be determined. This helps to establish the characteristics of the formation traversed by the wells, and to increase the efficiency in the exploration and production of the hydrocarbons contained in the formation.

In some embodiments of the invention, the presence or absence of particles from the first set or second set of tracer particles in fluid produced from the production well is determined using fluid while the fluid is still within the production wellbore. In other embodiments, fluid with magnetically extracted tracer particles is removed from the production wellbore and analyzed externally.

In various embodiments of the invention, magnetic tracer particles in a fluid are concentrated by an array of magnets in a collector-reader. The directions of magnetization of adjacent magnets in the array are oriented to create regions of high magnetic field gradient in the fluid near the array. Tracer particles collect in these regions of high field gradient and are captured for analysis. A reader excites the ID elements in the captured particles and detects the particle excitation signature emitted by the excited particles. The tracer particles can then be identified from the particle excitation signature.

In one embodiment, the collector-reader includes a magnet array configured as a rotating disk inside a wellbore. Magnetic particles attracted to the edge of the disk by the magnet array are scooped off by a stopper as the array rotates. A reader excites the ID elements in the particles concentrated by the stopper and detects the resulting emitted signatures from the tracer particles. In a specific embodiment, X-ray fluorescence is employed to analyze the collected particles.

In another embodiment, the collector-reader includes a magnet array configured as a rotating collar external to the wellbore. Magnetic particles attracted to the inside of the collar by the magnet array are concentrated by a v-shaped stopper as the array rotates. A reader excites the ID elements in the concentrated tracer particles and detects the resulting emission signature. In specific embodiments, optical fluorescence is employed to analyze the collected particles.

In another embodiment, the collector-reader includes a linear array of magnets surrounded by a sheath. The linear array is inserted into the wellbore and particles in the fluid are attracted by the magnet array and captured by the sheath. The captured particles are removed from the wellbore and analyzed by an external reader. The reader excites the ID elements in the particles and detects the resulting emission signature identify the origin of the tracer particles.

In various embodiments of the collector-reader, the magnet configuration in the array may include permanent magnets with opposite polarities in adjacent magnets. In other embodiments a Halbach array may be employed.

BRIEF DESCRIPTION OF THE DRAWINGS

The foregoing features of embodiments will be more readily understood by reference to the following detailed description, taken with reference to the accompanying drawings, in which:

FIG. 14 is a cross-sectional side view of a collector-reader using a linear array of permanent magnets in another embodiment of the invention; and FIG. 15 is a cross-sectional end view of the collector-reader linear array in the embodiment of FIG. 14.

DETAILED DESCRIPTION OF SPECIFIC EMBODIMENTS

In various embodiments of the invention, a method is provided for observing a subterranean reservoir penetrated by a production wellbore and two or more injection wellbores. A first set of tracer particles is delivered to the reservoir by one injection wellbore, while a second set of tracer particles is delivered to the reservoir via a second injection wellbore. The first set of tracer particles includes a first identification element while the second set of tracer particles includes a second identification element. The presence or absence of particles from the first set or second set of tracer particles in fluid produced from the production well is determined by X-ray fluorescence spectroscopy using the identification elements in the production fluid. The fluid flow (or absence thereof) from a particular injection well and the production well can thus be determined. In preferred embodiments of the invention, this identification can be accomplished using produced fluid while the fluid is still in the production well, by using XRF through an X-ray transparent window. In other embodiments, the tracer particles including magnetic material are concentrated from the produced fluid by using magnetism, fluid mechanics, mechanical systems, or any combination of them, for identification by X-ray fluorescence spectroscopy through an X-ray transparent window, while still in the pipe. In still further embodiments, the fluids or magnetically concentrated particles are removed from the oil stream and analyzed outside the oil pipe. In still further embodiments, optical fluoroscopy or another analogous technique is employed to identify the identification elements in the tracer particles.

Figure 1:
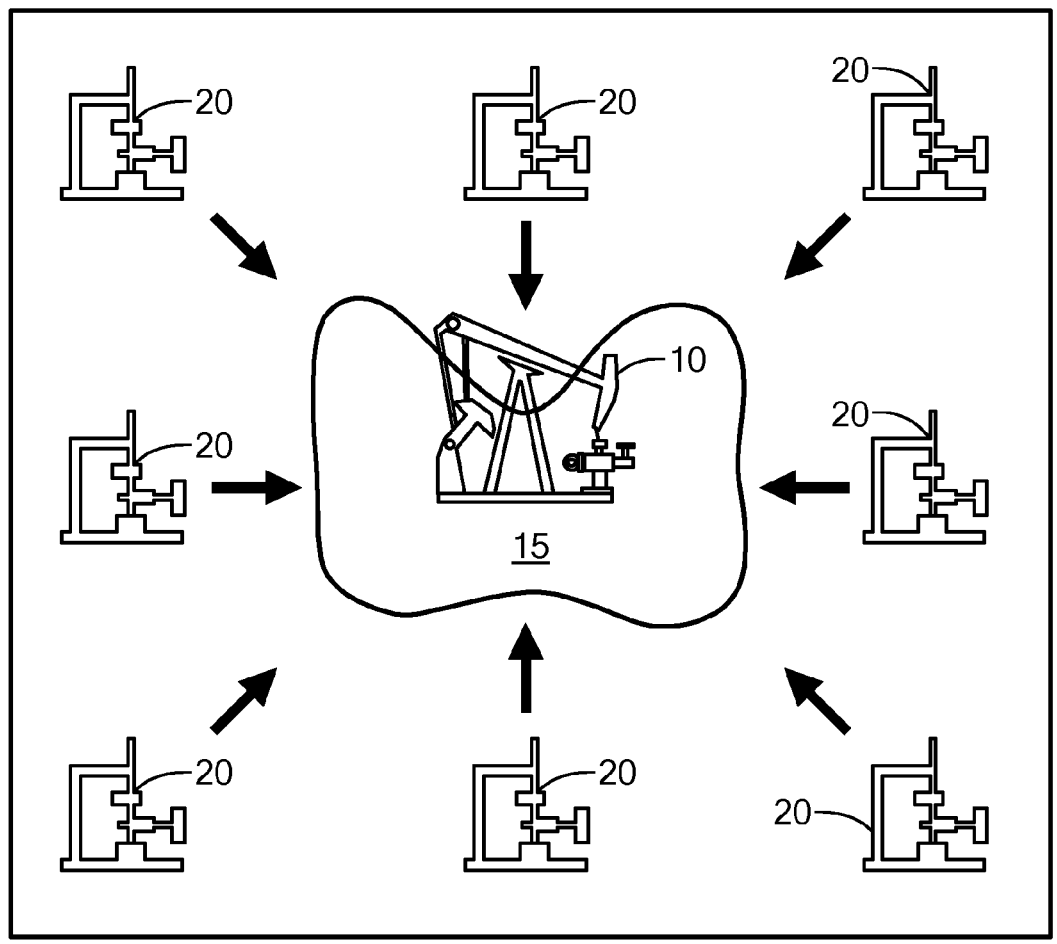
FIG. 1 shows schematically a production wellbore surrounded by a number of injection wellbores in an embodiment of the invention.
Figure 2:
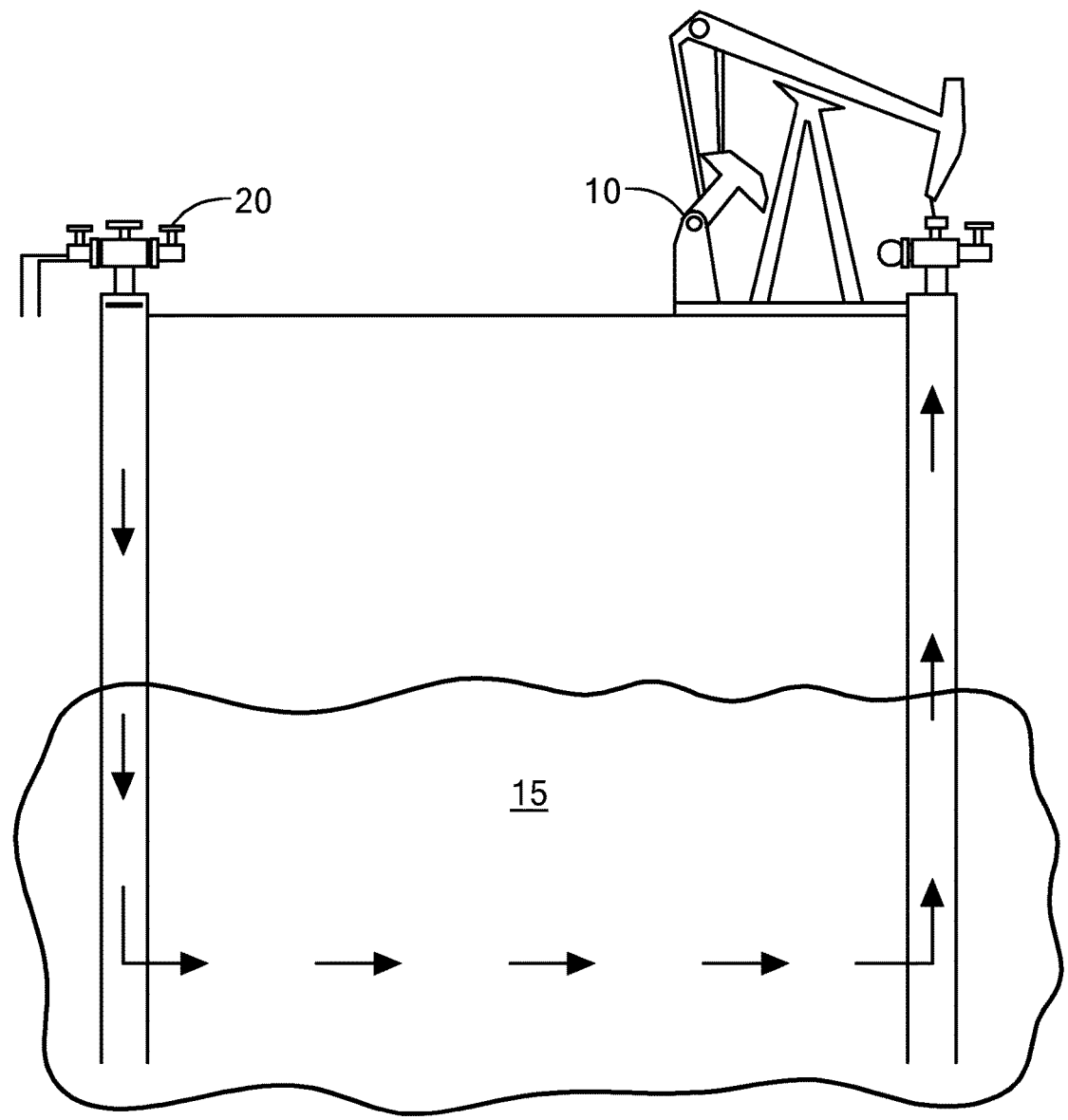
FIG. 2 shows the flow of fluid from one of the injection wellbores through the subterranean reservoir to the production wellbore in the well field of FIG. 1.

FIG. 1 shows schematically a production wellbore 10 surrounded by a number of injection wellbores 20. The injection wellbores 20 may be arranged in the periphery of a number of producing wells 10. Each injection wellbore 20 may inject fluid into a subterranean reservoir 15. The fluid injected into one or more injection wellbores may flow through to the production wellbore 10. FIG. 2 shows the flow of fluid from one of the injection wellbores 20 through the subterranean reservoir 15 to the production wellbore 10. Thus, fluid produced from the production wellbore may contain fluid injected into one or more injection wellbores along with other fluids extracted from the reservoir.

Figure 3:
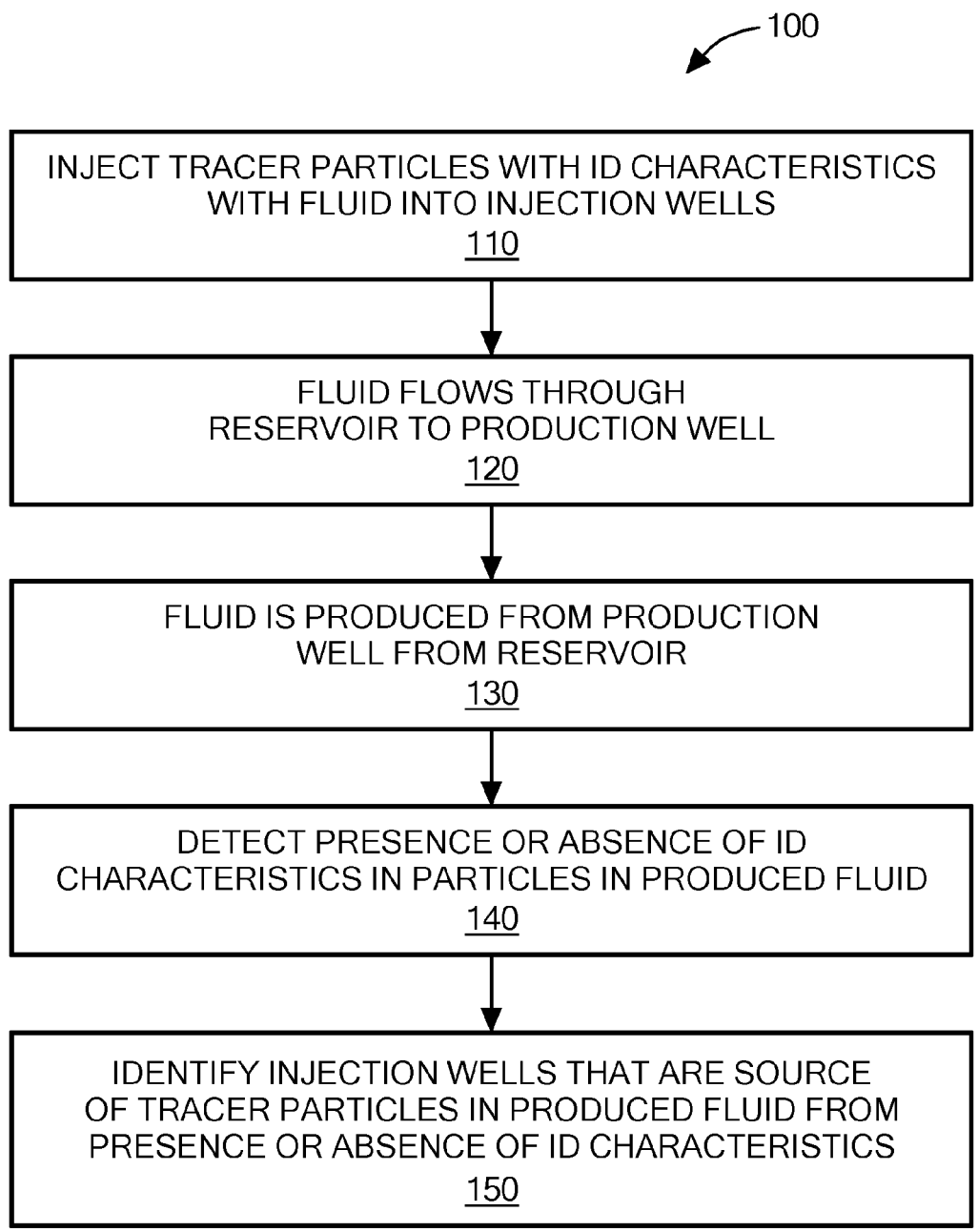
FIG. 3 shows a process of identifying an injection wellbore that is a source of fluid in produced fluid from a production wellbore, according to an embodiment of the present invention.

In a preferred embodiment of the invention, as shown in FIG. 3, a process 100 for determining source(s) of fluid produced from a production wellbore 10 is provided. Tracer particles are inserted 110 into injection wellbores along with fluid. Identification characteristics of the tracer particles inserted into a particular injection wellbore differ from the identification characteristics of tracer particles injected into any of the other injection wellbores 20. Injected fluid carrying the tracer particles flows 120 down the injection wellbores and into the subterranean reservoir 15. Fluid is subsequently produced 130 from the production wellbore and analyzed to determine 140 the identification characteristics of tracer particles that are present in the production fluid. Matching the identification characteristics of tracer particles in the production fluid with the ID characteristics of tracer particles injected into each individual injection wellbore allows identification of the specific injection well or wells from which the tracer particles entered the reservoir 150.

Figure 4C:
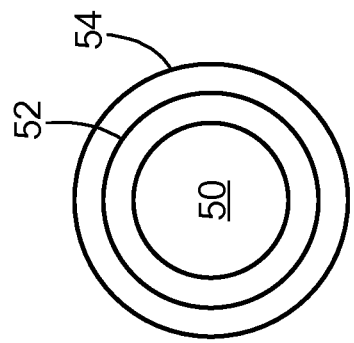
FIGS. 4A-4C shows tracer particles that may be used in the embodiment of FIG. 3.
Figure 4B:
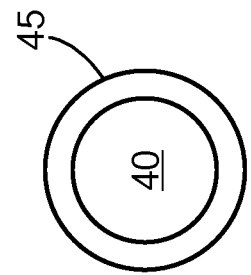
Figure 4A:
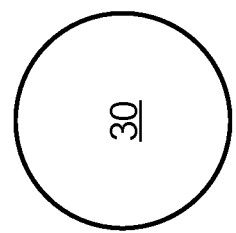

In specific embodiments of the invention, the tracer particles can be micro- or nano-tags, which have a magnetic component (e.g., a ferrite or magnetic oxide) and one of a number of distinguishable identification ("ID") elements which allow multiple sources to be distinguished, or the fractional contribution of each source to be quantified. FIGS. 4A to 4C show illustrative examples of the tags. FIG. 4A shows a tracer particle 30 with mixed ferrite that is both magnetic and contains an ID element. FIG. 4B shows a tracer particle with a magnetic core 40 surrounded by a layer 45 containing an ID element, while FIG. 4C shows a tracer particle with a magnetic core 50, ID element layer 52 and protective outer shell 54. The protective outer shell can protect against high temperature and/or pressure in subsurface oil producing strata and may be, for example without limitation, $TiO_2$ or $Al_2O_3$. Well known ferrites contain various elements that determine their magnetic properties. These elements include, but are not limited to: Ni, Y, Mn, Zn, Cd, Mg, Al, Co, and Cu. The magnetic component of each tracer particle 30, 40, 50 allows for concentration or extraction of the particles from the produced fluid stream using magnetic field gradients for analysis, in various embodiments of the invention. (Note: details of magnetic tracer particle concentration and extraction in various embodiments of the invention are presented below.) Thus concentrated, detection of the tracer particles is easier than if these particles were uniformly distributed in solution or suspension in the production fluid. In other embodiments, the ID elements of the tracer particles can be read in real time directly in the fluid that carries the tracer particles through the producing wellbore 10. In various embodiments, tracer particles can range in diameter, for example, from 10 nm to 30 nm; in other embodiments tracer particles can range from 0.1 um to above 10 um.

In preferred embodiments of the invention, X-ray fluorescence spectroscopy ("XRF") is used to detect the presence or absence of specific ID elements in tracer particles in the produced fluid. XRF is a sensitive, non-contact technique for measuring elemental composition of samples. (XRF is described in detail in *X-Ray Fluorescence Spectrometry*, 2nd Edition, by Ron Jenkins, published by Wiley, June 1999. XRF is also described in detail in *Handbook of Practical X-Ray Fluorescence Analysis*, Beckhoff, B., Kanngießer, B., Langhoff, N., Wedell, R., Wolff, H. (Eds.), published by Springer in 2006. Each of these references is incorporated by reference herein in its entirety.) The produced fluid from the production well 10 is interrogated with X-rays. The X-ray spectrum of the interrogated fluid sample includes various peaks that correspond to specific elements present in tracer particles that are in the produced fluid. The ID element(s) in each set of tracer particles is chosen so that the XRF signature of each set of particles can be distinguished from the signature of every other set of tracer particles used in the subterranean reservoir 15. Because each set of tracer particles is injected into one injection wellbore only, detection of the XRF signature of that particular set of tracer particles indicates that fluid from the particular injection well contributed to the produced fluid. Depending on X-ray cross-section, the various elements are detectable at different detection limits. Elements or oxides with a low detection threshold are preferred for the ID elements. Based on the atomic elements which are detectable at less than 150 parts per million, in specific embodiments of the invention, Ti, V, Cr, Mn, Co, Ni, Cu, Zn, Ba, Sr, Y, Zr, Nb, Mo, Hf, or Ta may be chosen for ID elements. In a preferred embodiment of the invention, a single atomic element or oxide is used as the ID element for a particular set of tracer particles. The strength of the XRF signature of a particular ID element can help determine the contribution of the fluid from a particular injection well to the produced fluid. Selection of these elements can be based, in various applications, on the cost, toxicity and chemical stability of the oxides in the wellbore environment. Oxides of several of these elements are extremely stable and would make good protective layers, e.g., $Cr_2O_3$, $Y_2O_3$, $ZrO_2$, $HfO_2$.

In other preferred embodiments of the invention, one or more of: atomic absorption, atomic spectroscopy, neutron activation, optical fluorescence, inductively coupled plasma mass spectrometry, and X-ray photo-electron spectroscopy are used to determine the ID element(s) in a tracer particle. The ID element in the particle is selected according to the analytical technique(s) to be used. For example, if optical fluorescence is used as the analytical technique, quantum dots may be used as the ID element that is combined with the magnetic material in the tracer particle. The analysis may take place with the fluid sample in the pipe, or in some cases, a fluid sample may be removed from the pipe for analysis external to the pipe.

Magnetic Tracer Particle Collection and Analysis

In various preferred embodiments of the invention, magnetic tracer particles in a fluid are concentrated by an array of magnets, which may be permanent magnets. The directions of magnetization of adjacent magnets in the array are oriented to create regions of high magnetic field gradient in the fluid near the array. Tracer particles collect in these regions of high field gradient and are captured for analysis. A reader excites the ID elements in the captured particles and detects the particle excitation signatures emitted by the excited particles. The tracer particles can then be identified from the particle excitation signatures.

Figure 5:
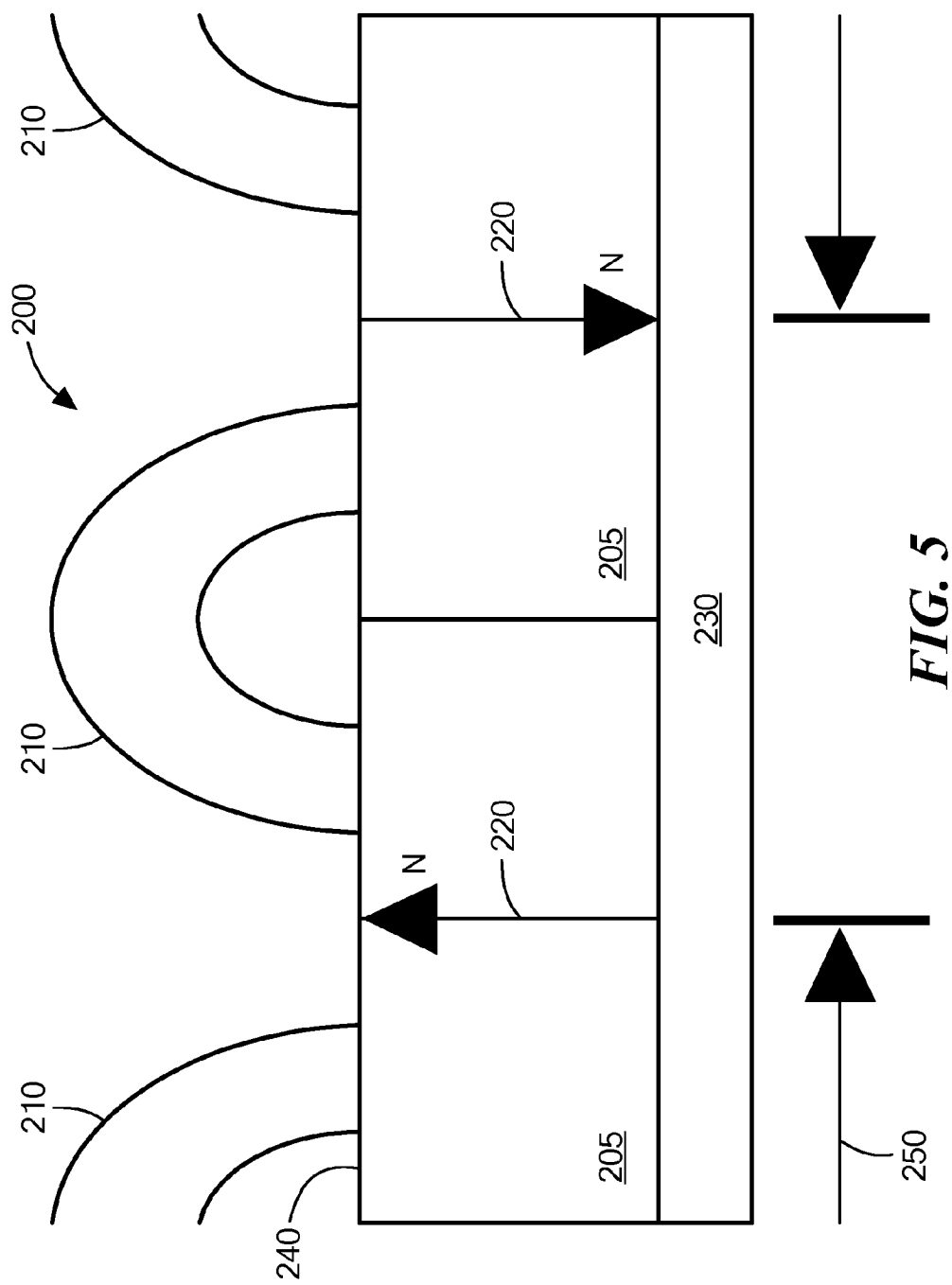
FIG. 5 is a diagram showing the magnetic flux lines in a portion of an array of permanent magnets where adjacent magnets having opposite polarities.

FIG. 5 shows a portion of an array 200 of alternating polarity permanent magnets 205 on a soft magnetic flux return 230. The magnetic flux is shown by the curved lines 210 with the maximum gradient at the interface between magnets of opposite polarity. (The polarity of the magnets is as shown by vectors 220.) Magnetic particles suspended in fluid near the magnets' surface 240 will collect preferentially at sites of higher magnetic flux gradient. The force on a magnetic particle in a magnetic field gradient $\nabla B$ is $$F = m \cdot \nabla B$$

where m is the magnetic dipole moment of the particle. For common soft ferrites, the saturation magnetization is on the order of $0.2*10^6$ A/m, with a relative permeability of 100-1000. Assuming a relative permeability of 100, a field of only 2000 A/m (equivalent to 25 Gauss) will saturate the particle magnetization. Given the strong fields available from modern permanent magnets, we can assume for simplicity that saturation magnetization is achieved. The force on the particle and achievable drift velocity through the fluid is proportional to the magnetic field gradient. For an array of alternating polarity permanent magnets (e.g. SmCo or NdFeB) with a characteristic spacing or period of $L_{mag}$ 250 the field gradient is then approximately $2*B_0/L_{mag}$. For a spherical particle of diameter d, traveling through a fluid of viscosity μ, the friction factor (ratio of force to velocity) $f = 3\pi\mu d$. Thus, for a given particle size and magnet spacing, the particle velocity can be derived.

In various embodiments of the invention, a variety of collector-reader implementations can take advantage of magnetic concentration and collection of magnetic tracer particles using magnet arrays as described below.

I. Magnet Array Disk Internal to Fluid-Filled Pipe.

Figure 6:
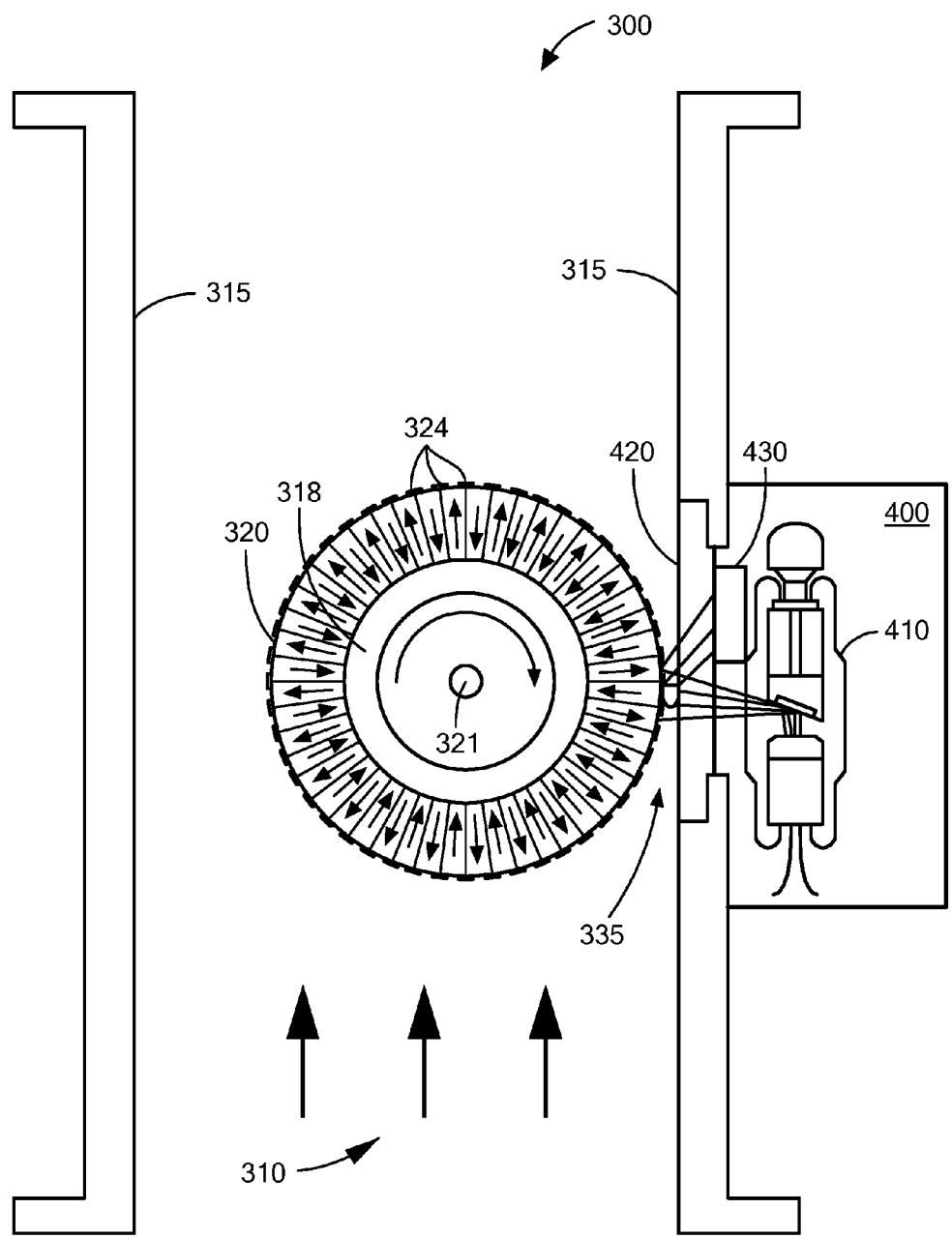
FIG. 6 is a cross-sectional view of a collector-reader apparatus situated in a wellbore, according to an embodiment of the invention.
Figure 7:
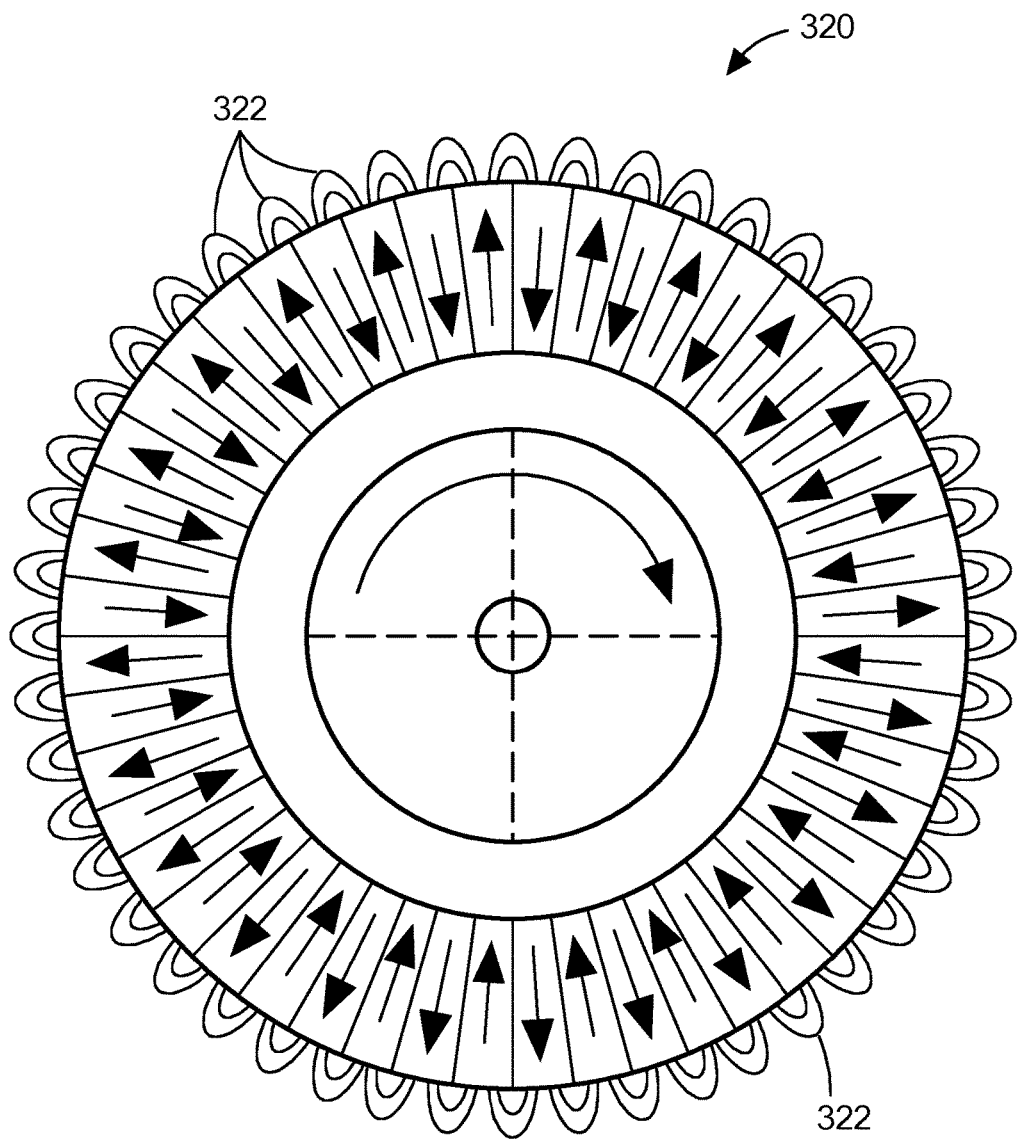
FIG. 7 shows the magnetic flux lines in an array of permanent magnets configured as a rotating disk in the embodiment of FIG. 6.
Figure 8:
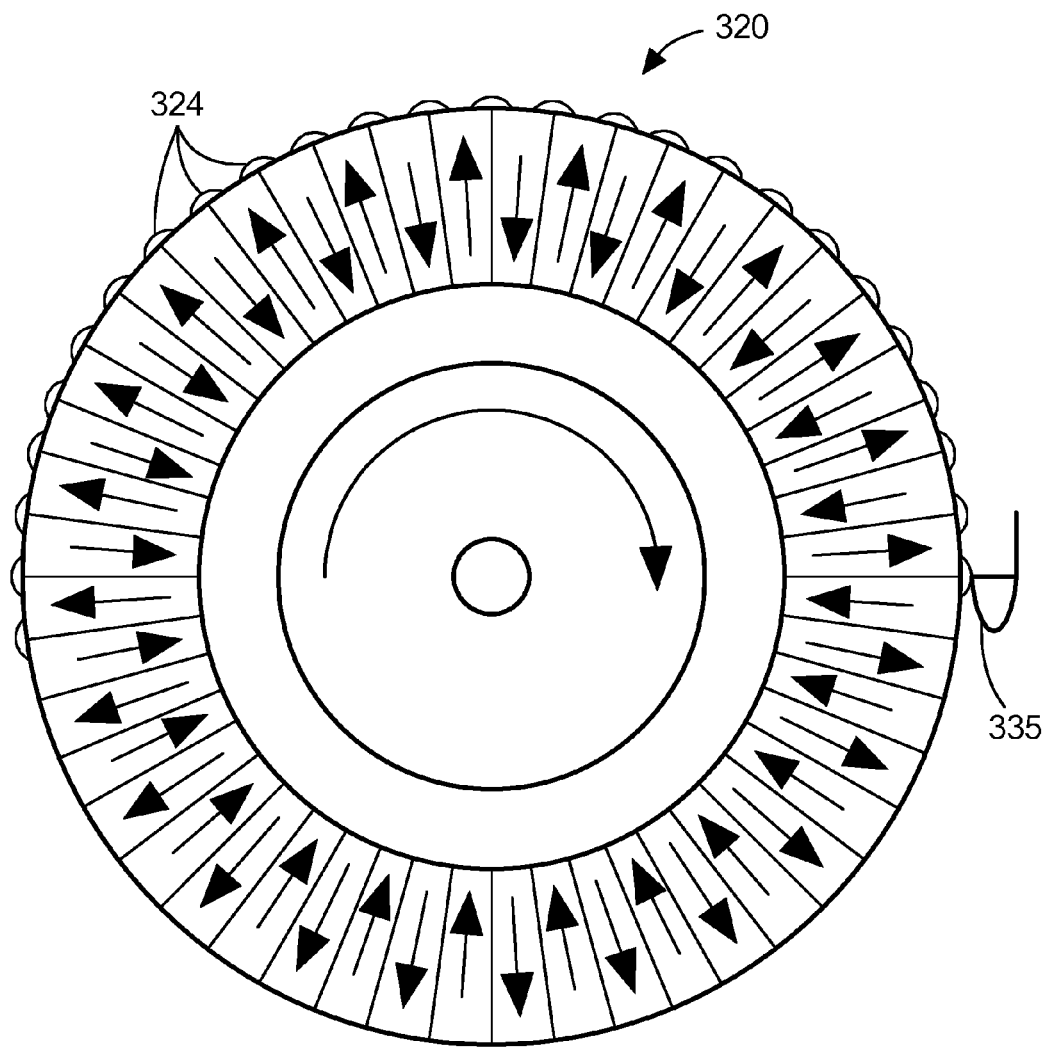
FIG. 8 shows tracer particles collected on the edge of the disk of FIG. 7 in areas of high magnetic flux gradient and a stopper that concentrates the collected particles as the disk rotates.

In a preferred embodiment of the invention, as shown in overall cross section in FIG. 6, a collector-reader apparatus 300 is employed to identify ID elements in tracer particles. A rotating disk array 320 of permanent magnets is installed in the wellbore 315. The disk spins on an axis 321 perpendicular to the plane of the drawing. The disk attracts magnetic tracer particles 324 as fluid 310 flows by the array and as the array spins. As pictured in FIG. 7, the magnets in this array alternate in magnetization direction as shown by the arrows. (In FIGS. 6-9, each magnet in the array is identified by an arrow showing its magnetization direction.) A soft magnetic flux return 318 is provided in the disk. These magnets create areas of maximum magnetic flux gradient 322 between adjacent magnets. Magnetic tracer particles are preferentially attracted to these areas of maximum gradient 322. As shown in FIG. 8, a stopper 335 is provided to collect, and thus to concentrate, the tracer particles by stripping the collected particles 324 from the disk as the disk spins. In this embodiment, the stopper 335 is shaped as a scoop but other shapes for the stopper are also possible, e.g., v-shaped. FIG. 8 is an enlarged side view of the disk array 320 showing the areas 324 where magnetic particles preferentially collect on the edge of the disk. Particles which have been stripped off and held by the stopper 335 as the disk spins are also shown. These concentrated tracer particles can then be analyzed.

Returning to FIG. 6, a reader 400 is provided for the collector-reader apparatus 300. In this embodiment, the reader 400 combines an X-ray tube 410 source that emits X-rays and an X-ray detector 430. The X-rays strike the magnetic tracer particles in the stopper 335 through an X-ray transparent window 420 in the wall of the wellbore 315. When excited with X-rays, these tracer particles can emit secondary X-rays with wavelengths characteristic of the ID elements in the magnetic tracer particles. These secondary X-rays are received by the detector 430 and an electronic signature is generated that is characteristic of the ID elements present. Thus, the composition of the tracer particles can be determined.

Figure 9:
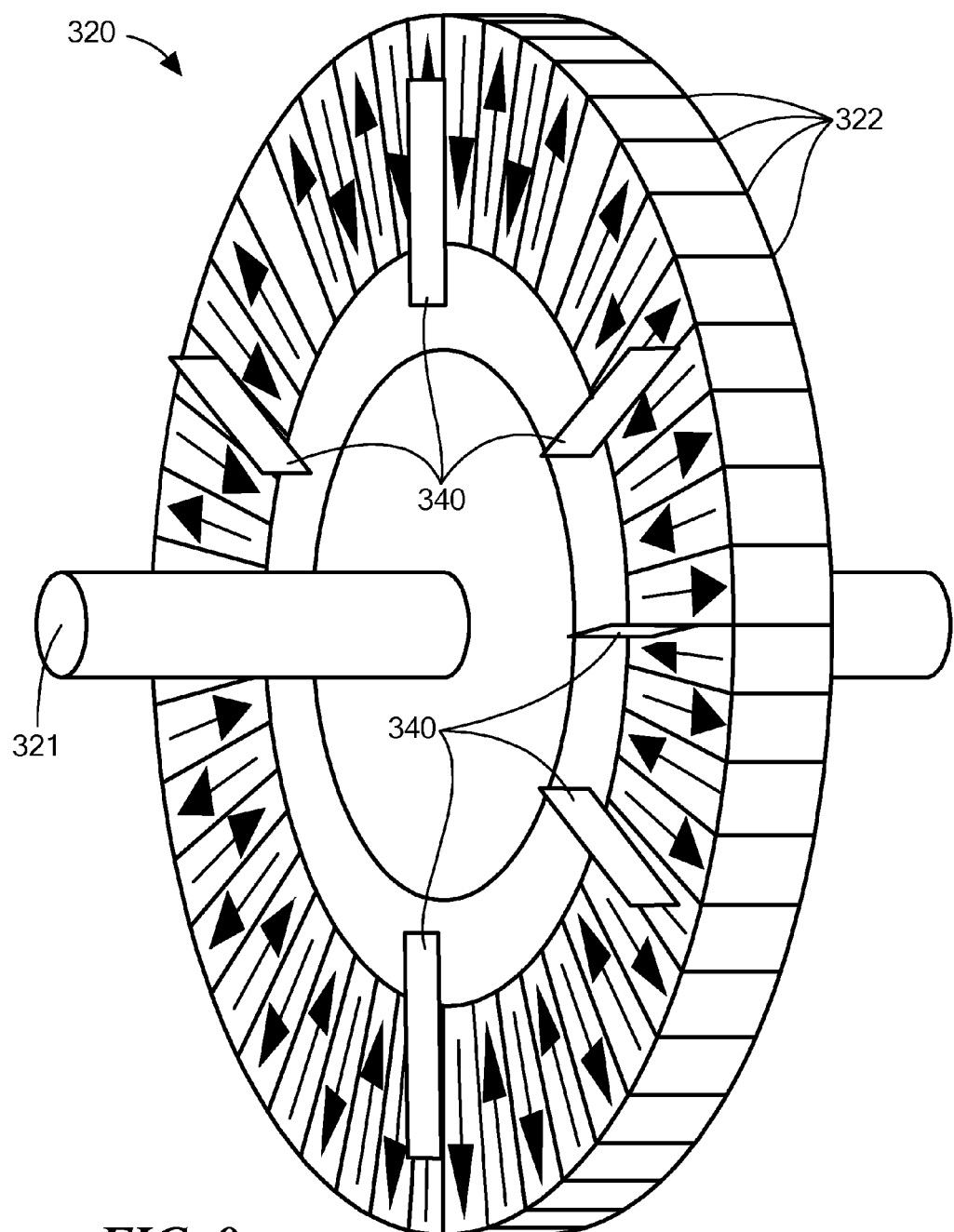
FIG. 9 is a perspective view of the rotating disk of FIG. 7 showing fins that rotate the disk when impacted by a fluid flow.

FIG. 9 is a perspective view of the disk 320, in an embodiment of the invention, where fins 340 are provided on the sides of the disk. As fluid 310 flows past the disk striking the fins, the disk rotates. Note that fins 340 may also be provided on the side of the disk not shown in FIG. 9.

In other preferred embodiments, the reader 400 in FIG. 6 may employ any technology for source 410 and detector 430 that can excite the collected magnetic tracer particles to emit a characteristic signature that can be detected, e.g., optical fluorescence, etc. Likewise, other magnet array configurations may be used, such as a Halbach array. (The Halbach configuration is described below.) Further, in other embodiments, any array configuration of permanent magnets whose magnetization direction is varied so as to create regions of high magnetic flux gradient in the fluid near the disk may be used to collect the tracer particles.

II. Magnet Array Disk External to Fluid-Filled Pipe

Figure 10:
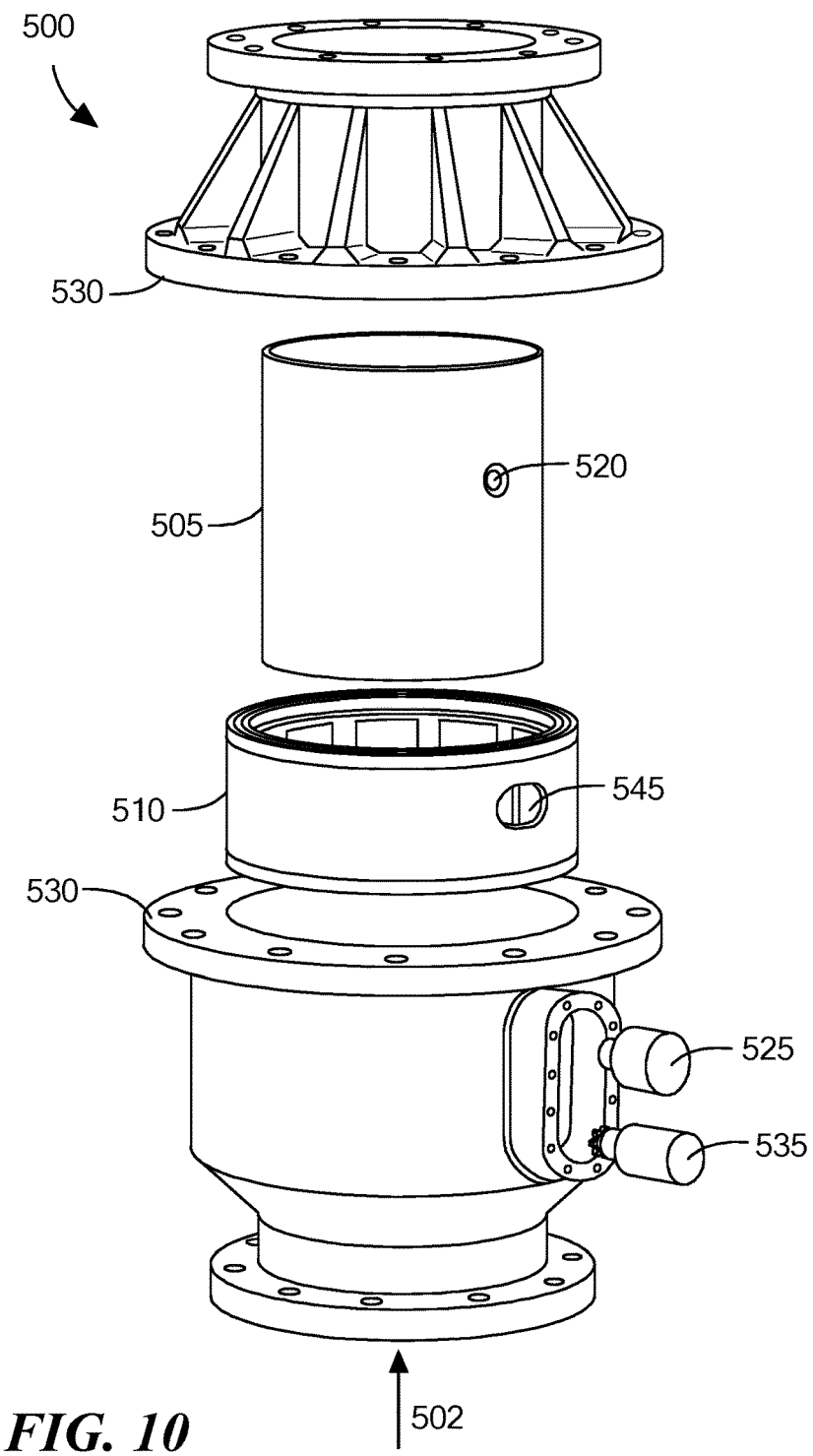
FIG. 10 is an exploded perspective view showing a collector-reader where the magnet array is configured as a collar external to the wellbore, in an embodiment of the invention.

In another preferred embodiment of the invention, as shown in an exploded perspective view in FIG. 10, a collector-reader apparatus 500 is employed to identify ID elements in tracer particles. A thin section of pipe of non-magnetic material 505 (e.g., Ti alloy) replaces a conventional pipe section in the wellbore. A rotating array 510 of permanent magnets surrounds this pipe section as a collar. This array rotates about the pipe section 505, driven by a collar actuator motor through a port 535, with the motor not shown. The axis of the non-magnetic pipe section 505 and the axis of the collar 510 coincide. A housing 530 is provided to contain the above components. Fluid 502 flows as shown in FIG. 10.

Figure 11:
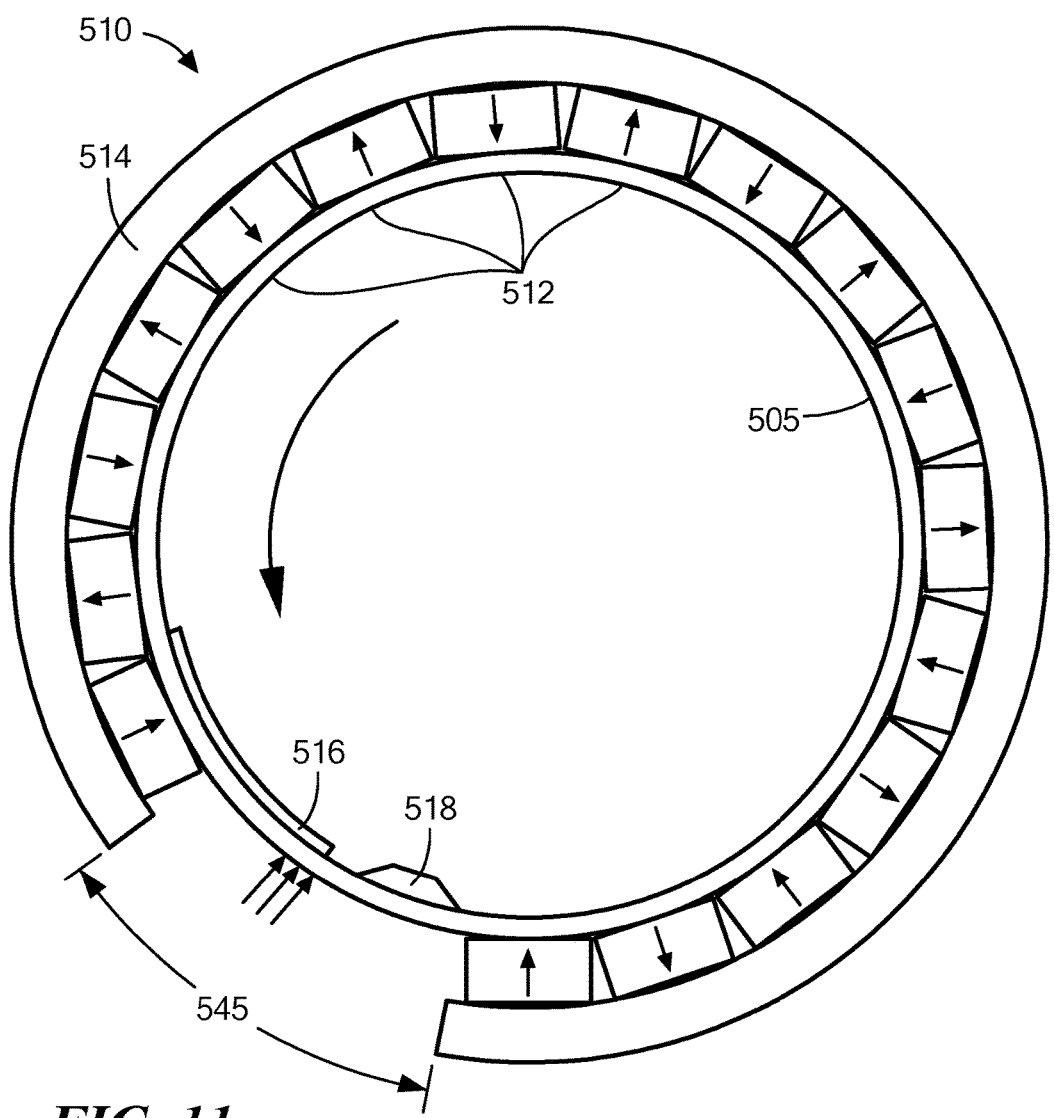
FIG. 11 shows a cross-section of the magnet array collar of FIG. 10, where the array includes magnets of alternating polarity.
Figure 12:
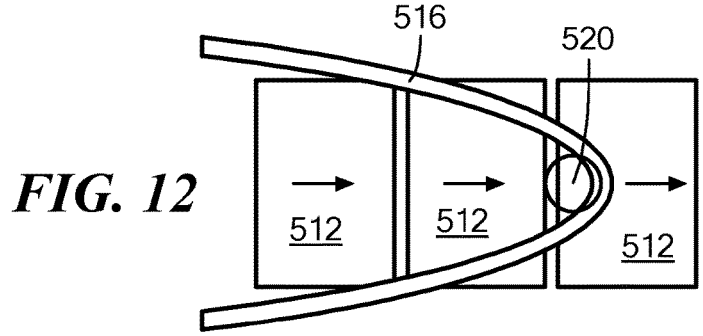
FIG. 12 is a cross-section of the stopper portion of the embodiment shown in FIG. 10.

FIG. 11 is a top down view of a configuration of the magnetic array collar 510 in this embodiment. As shown in FIG. 11, the magnets 512 in this array alternate in magnetization direction as shown by the arrows. A soft magnetic flux return 514 is provided in the collar. These magnets create areas of maximum magnetic flux gradient between adjacent magnets, interior to the collar. Magnetic tracer particles are preferentially attracted to these areas of maximum magnetic flux gradient and collect on the inner surface of the non-metallic pipe 505 near these magnet junctions as fluid 502 flows past the level of the collar 510. A v-shaped stopper 516 is attached to the inner wall of the non-metallic pipe 505. This stopper is shown in cross-section in FIG. 12. As a collar actuator motor (not shown) rotates the collar on its axis, magnetic tracer particles collected on the inner pipe wall rotate toward the v-shaped stopper 516. The "v" of the stopper 516 concentrates the tracer particles under a window 520 in the pipe, for analysis.

A particle cleaner 518 is provided to remove particles from the stopper 516, after analysis. The particle cleaner is a protuberance on the inner wall of the non-metallic pipe section 505, as shown in FIG. 11. When the collar is rotated by the motor in a direction reverse to the collection rotational direction, particles in the stopper move along the inner wall of pipe 505, leaving the stopper 516. Eventually these particles hit the bump 518 on the pipe wall and are dispersed back into the fluid. The collector-reader apparatus 500 is thus prepared for further particle collection and analysis.

A reader 400, as described in paragraphs 37 and 39, is provided. A port 525 is provided in the housing 530 for entry of excitation energy (e.g., X-rays) from the reader source and for channeling the resultant excitation signature to a detector. (Neither source nor detector are shown here for clarity.) A window 520 in the non-metallic pipe section 505 is provided for energy access and energy egress from/to the particles collected by the v-shaped stopper. A corresponding window 545 in the rotating collar 510 rotates over the window 520 once per collar revolution, thus allowing energy access and egress through the collar. Analysis of the signature to identify the ID elements in the tracer particles is as described above.

Figure 13:
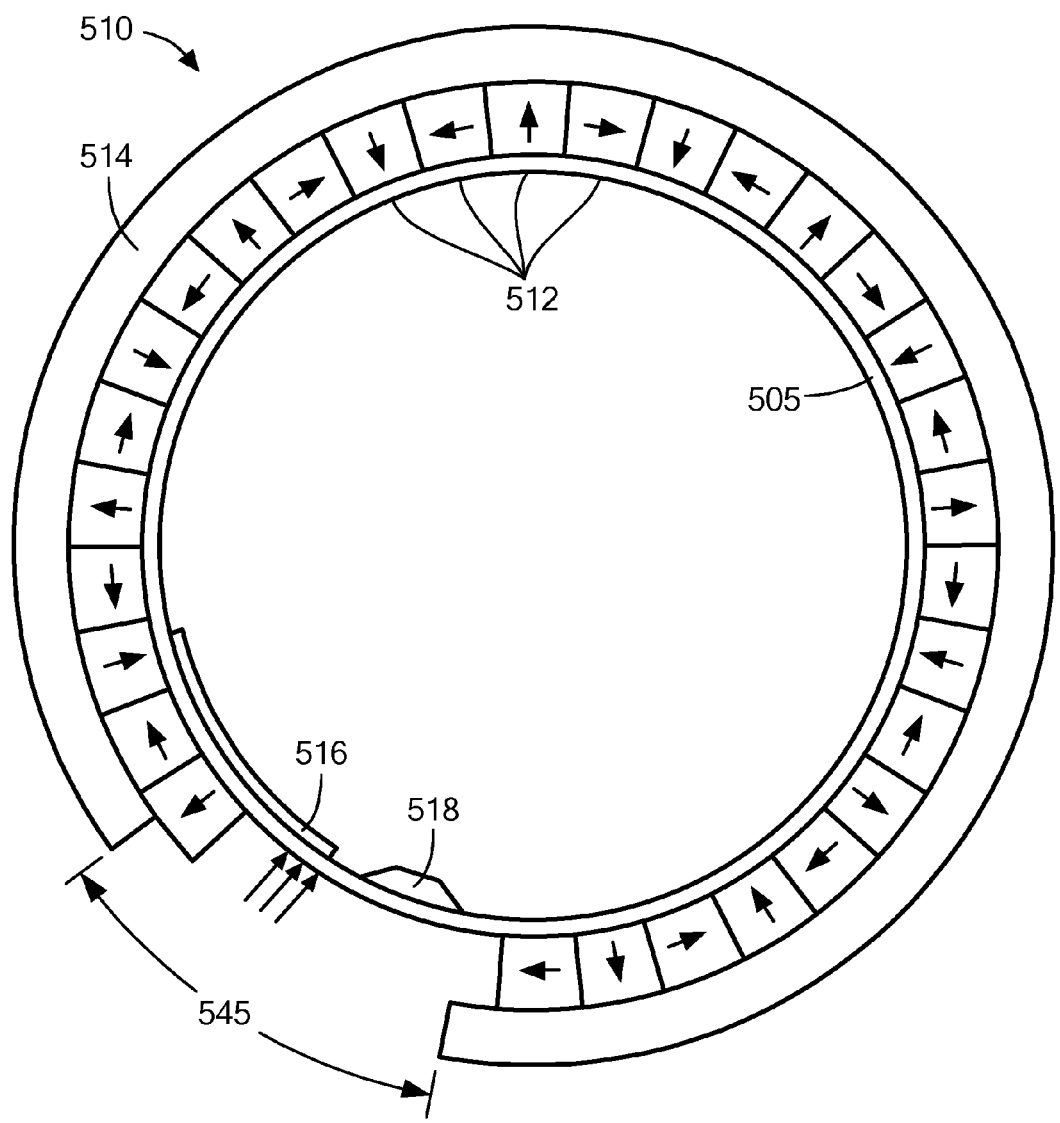
FIG. 13 shows a cross-section of an alternative magnet array collar configuration for the embodiment of FIG. 10, where the array is configured as a Halbach array.

In another preferred embodiment, a Halbach array is used as the collar magnet array 510, as shown in FIG. 13. In this embodiment, the magnets in the array alternate in magnetization direction as shown. This magnet configuration maximizes the flux gradient on the inner surface of the magnet array. Thus, magnetic particle collection is enhanced. Other features of the collar array 510 are the same as in the collar array shown in FIG. 11, which is described above.

III. Removable Linear Array

In a further preferred embodiment of the invention, as shown in side cross section in FIG. 14, a collector-reader apparatus 600 is employed to identify ID elements in tracer particles. A linear array 605 of permanent magnet disks 620, 621 is installed in a port in the side of the wellbore. The magnet disks alternate in magnetization direction (as shown by arrows) from outward poled 620 to inward poled 621. These magnet disks can be loaded onto a soft magnetic rod 610. These magnets create areas of maximum magnetic flux gradient between adjacent magnets. Magnetic tracer particles are preferentially attracted to these areas of maximum gradient and collect at the junctions between magnets on the exterior of the array. The linear array 605 of magnet disks can slide into a sheath 630, such as a polymer sheath, that encases the array. The sheath 630 can trap magnetic tracer particles that are attracted to the array as fluid flows past the array 605. These particles can then be removed from the wellbore for analysis. FIG. 15 shows a cross-section of the linear array from the end of the array.

An external reader is provided (not shown). Particles removed from the wellbore are analyzed as described in paragraphs 37 and 39. Because the particles are removed from the wellbore, the reader can take on any convenient form factor.

Applications

Various embodiments of the invention can include one or more of the following features or be applied in one or more application methods:

1. Certain modifications of the tracer particles' surface chemistry can help users to infer information about the chemical characteristics of the fluids trapped in the formation through which the particles have traveled from the injecting well to the producing well.

2. The tracer particles can be designed to last for long periods of time, so they can be used to track the flow of fracking fluids into aquifers. This will enable better tracking of environmental impact of fracking fluids, especially after long periods of time.

3. One of the pieces of information that the tracer particles can encode in the ID elements can be the date when they were injected into the subterranean reservoir. The arrival date for the particle in the production well and the identity of the source injection well can allow the determination of the flow rate of the injected fluid through the formation, as well as allow mapping the geometry of fluid flow paths.

4. In other embodiments, this identification method can be used in sand control. After the gravel packers or mesh are installed for sand control, the tags that come from wellbores where the tracer particles have been injected could be trapped in the packers. A reading device can be permanently placed next to the completions packer and can be used to detect the source of the tracer particles' tags.

5. In another embodiment, also related to sand control, the reading device, e.g., a Wireline tool, can be lowered into the producing well next to the gravel packers or mesh that are performing the sand control, so that the origin of the produced oil or gas can be determined.

6. In various embodiments, this technology can be used in the utilities industry to determine the path of street level water leaks. This can be done by injecting tracer particles into several potential sources, and by reading the ID elements that come out of the leak on the street.

7. In some embodiments, these tracer particles and the process described above can be used to track the path of fluids inside manufacturing plants in which mixing of fluids plays an important role.

8. In some embodiments, these tracer particles and the process described above can track the contribution of smaller rivers to larger rivers. This is of particular importance in agricultural management of water sources.

9. To improve logistics of raw materials, these tracer particles can be placed in bulk materials from different towns or countries. When the raw material from different sources is mixed, many times one wants to know or verify where the raw materials come from. The process and devices described above can be used to track and authenticate the origin of the materials.

10. The process and devices described above can find leaks from one of multiple fluid streams to another fluid stream.

The embodiments of the invention described above are intended to be merely exemplary; numerous variations and modifications will be apparent to those skilled in the art. For example, while embodiments of the invention have been described as employing permanent magnets to attract tracer particles using magnetic fields, other methods of generating magnetic fields, such as electromagnets, etc. may be used in other embodiments of the invention. All such variations and modifications are intended to be within the scope of the present invention. Embodiments of the invention may be described, without limitation, by the claims that follow.

What is claimed is:

1. A collector-reader for analyzing magnetic particles in a fluid that is moving with respect to the collector-reader comprising:
    an array of magnets whose magnetization direction is varied so as to create regions of high magnetic field gradient in the fluid, wherein the array of magnets is configured to be suspended in the fluid, and wherein the array of magnets is configured as a disk with an axis and disk fins that spin the disk on the axis when impacted by the fluid;
    a stopper configured to concentrate spatially the particles attracted to the array; and
    a reader including a source configured to excite the particles concentrated by the stopper and a detector configured to capture a particle excitation signature emitted by the magnetic particles.

2. The collector-reader of claim 1, wherein adjacent magnets in the array have opposite magnetization polarity or are configured as a Halbach array.

3. The collector-reader of claim 1, wherein the source excites the particles with X-rays and the detector measures the resulting particle X-ray fluorescence.

4. The collector-reader of claim 1, further including a window transparent to X-rays adjacent to the stopper.

5. The collector-reader of claim 1, wherein the source excites the particles optically and the detector measures the resulting optical fluorescence.

6. The collector-reader of claim 1, wherein the source excites the particles and the detector measures particle excitation using one or more of:
    X-ray fluorescence,
    optical fluorescence,
    atomic absorption,
    atomic spectroscopy,
    neutron activation,
    inductively coupled plasma mass spectrometry, and
    X-ray photo-electron spectroscopy.

7. The collector-reader of claim 1, wherein the stopper is v-shaped.

8. The collector-reader of claim 1, wherein the reader is at least 10 feet from the array.

9. A method for making observations of a subterranean reservoir penetrated by a production well including a pipe producing a fluid and by at least two injection wells comprising:
    delivering a first set of tracer particles to a first subterranean location via a first injection well and delivering a second set of tracer particles to a second subterranean location via a second injection well;

producing fluid out of the reservoir via the production well, wherein producing the fluid includes concentrating tracer particles in the produced fluid using a collector comprising:
- an array of magnets positioned within the production well pipe, wherein adjacent magnets in the array have opposite magnetization polarity or the array is a linear array, the fluid moving with respect to the array, and
- a removable sheath configured to capture the particles magnetically attracted to the array and transfer them for analysis; and detecting the presence or absence of the first set of tracer particles in the produced fluid and detecting the presence or absence of the second set of tracer particles in the produced fluid, wherein the tracer particles each include a magnetic material and an identification element, the identification element in the first set of tracer particles differing from the identification element in the second set of tracer particles and wherein detecting the presence or absence of tracer particles is performed by detecting one or more identification elements using one or more of:

X-ray fluorescence spectroscopy,
atomic absorption,
atomic spectroscopy,
neutron activation,
optical fluorescence,
inductively coupled plasma mass spectrometry, and
X-ray photo-electron spectroscopy.

10. The method according to claim 9, wherein producing fluid out of the reservoir via the production well further includes concentrating tracer particles in the produced fluid using magnetic extraction.

11. The method according to claim 10, wherein producing fluid out of the reservoir via the production well further includes concentrating tracer particles in the produced fluid using a collector comprising:
- an array of magnets, the fluid moving with respect to the array; and
- a stopper configured to concentrate spatially the particles magnetically attracted to the array.

12. The method according to claim 9, further including determining the proportion of fluid from the first injection well to fluid from the second injection well in the produced fluid by determining the proportion of the first set of tracer particles to the second set of tracer particles in the produced fluid.

13. A collector-reader for analyzing magnetic particles in a fluid that is moving with respect to the collector-reader comprising:

- an array of magnets whose magnetization direction is varied so as to create regions of high magnetic field gradient in the fluid, wherein the array of magnets is configured as a collar surrounding a non-magnetic section of a pipe, wherein an axis of the array and an axis of the pipe are coincident, and wherein the array is configured to rotate on its axis;
- a stopper configured to concentrate spatially the particles attracted to the array;
- a cleaner that removes magnetic particles from the stopper; and
- a reader including a source configured to excite the particles concentrated by the stopper and a detector configured to capture a particle excitation signature emitted by the magnetic particles.

14. The collector-reader of claim 13, wherein the cleaner is a protuberance on an inner surface of the non-magnetic section of the pipe.

15. A method for making observations of a subterranean reservoir penetrated by a production well including a pipe producing a fluid and by at least two injection wells comprising:

delivering a first set of tracer particles to a first subterranean location via a first injection well and delivering a second set of tracer particles to a second subterranean location via a second injection well;

producing fluid out of the reservoir via the production well; and detecting the presence or absence of the first set of tracer particles in the produced fluid and detecting the presence or absence of the second set of tracer particles in the produced fluid, wherein the tracer particles each include a ferrite or ferrous alloy magnetic material surrounded by a layer containing an identification element, the identification element in the first set of tracer particles differing from the identification element in the second set of tracer particles, wherein the layer is covered by a protective shell, and wherein detecting the presence or absence of tracer particles is performed by detecting one or more identification elements using one or more of:

X-ray fluorescence spectroscopy,
atomic absorption,
atomic spectroscopy,
neutron activation,
optical fluorescence,
inductively coupled plasma mass spectrometry, and
X-ray photo-electron spectroscopy.

* * * * *